United States Patent
Sundquist et al.

(10) Patent No.: US 6,567,704 B2
(45) Date of Patent: May 20, 2003

(54) MEDICAL ELECTRICAL LEAD AND METHOD OF USE

(75) Inventors: Steven Sundquist, Minnetonka, MN (US); Douglas S. Hine, White Bear Lake, MN (US); John L. Sommer, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/833,518

(22) Filed: Apr. 12, 2001

(65) Prior Publication Data

US 2002/0077685 A1 Jun. 20, 2002

Related U.S. Application Data

(60) Provisional application No. 60/257,025, filed on Dec. 20, 2000.

(51) Int. Cl.[7] .................................................. A61N 1/05
(52) U.S. Cl. ...................................... 607/119; 607/122
(58) Field of Search ................................ 607/119, 122; 606/27, 28; 604/96.01, 915, 916, 917, 918, 919, 920, 921; 600/431, 434, 435, 373, 585

(56) References Cited

U.S. PATENT DOCUMENTS

| | | | | |
|---|---|---|---|---|
| 4,355,646 A | | 10/1982 | Kallok et al. | 128/786 |
| 4,506,680 A | | 3/1985 | Stokes | 128/786 |
| 4,577,642 A | | 3/1986 | Stokes | 128/784 |
| 4,606,118 A | | 8/1986 | Cannon et al. | 29/825 |
| 4,711,251 A | | 12/1987 | Stokes | 128/784 |
| 4,718,423 A | * | 1/1988 | Willis et al. | 128/634 |
| 4,762,129 A | | 8/1988 | Bonzel | 128/344 |
| 4,784,892 A | * | 11/1988 | Rosenberg | 604/170 |
| 4,815,478 A | | 3/1989 | Buchbinder et al. | 128/772 |
| 4,922,912 A | | 5/1990 | Watanabe | 128/642 |

(List continued on next page.)

Primary Examiner—Irs S. Lazarus
Assistant Examiner—K. B. Rinehart
(74) Attorney, Agent, or Firm—Girma Wolde-Michael; Michael C. Soldner

(57) ABSTRACT

A medical electrical lead is disclosed having an inner lumen adapted to receive a stiffening member, and which is further adapted to deliver fluoro-visible media while the stiffening member is located within the inner lumen. According to one aspect of the invention, the stiffening member is a guide wire having an inner lumen. The inner lumen of the guide wire is used to deliver the contrast medium while the guide wire is in place within the lumen of the lead. In another embodiment, a stiffening member that is sized to occupy only a portion of the lumen of the lead is utilized. The non-occupied portion of the lumen is sized to be large enough to allow for the passage of fluoro-visible medium from an injection port at the proximal end of the lead to a delivery port at the distal end of the lead. According to one aspect of the invention, the lead includes a sealable member located at the distal end of the lumen of the lead to prevent the ingress of bodily fluids within this lead lumen. The sealable member includes an opening to allow the stiffening member to be advanced outside of the lead lumen. In one embodiment, the sealable member is a flexible membrane including at least one opening to allow for passage of the stiffening member. In another embodiment, the sealable member includes multiple flap-like structures that seal around a stiffening member advanced distally of the lead body. In yet another embodiment, a sealable member is located within an electrode at the distal tip of the lead. The electrode of this configuration is provided with diametrically opposed openings to allow the electrode to expand to allow for passage of the stiffening member. The lead of the current invention may further include an inflatable member that may be inflated prior to delivery of the contrast media to prevent the media from being flushed from a vessel before a venogram is obtained.

34 Claims, 14 Drawing Sheets

U.S. PATENT DOCUMENTS

| | | | | |
|---|---|---|---|---|
| 4,972,848 A | | 11/1990 | Di Domencio | 128/785 |
| 5,003,990 A | | 4/1991 | Osypka | 128/772 |
| 5,040,548 A | | 8/1991 | Yock | 128/898 |
| 5,087,244 A | | 2/1992 | Wolinsky et al. | 604/53 |
| 5,246,014 A | | 9/1993 | Williams et al. | 607/122 |
| 5,279,560 A | * | 1/1994 | Morrill et al. | 604/96 |
| 5,387,233 A | | 2/1995 | Alferness et al. | 607/126 |
| 5,395,352 A | * | 3/1995 | Penny | 604/256 |
| 5,569,296 A | * | 10/1996 | Marin et al. | 606/198 |
| 5,571,161 A | * | 11/1996 | Starksen | 607/122 |
| 5,584,873 A | | 12/1996 | Shoberg et al. | 607/122 |
| 5,755,766 A | | 5/1998 | Chastain et al. | 607/122 |
| 5,851,226 A | | 12/1998 | Skubitz et al. | 607/126 |
| 5,964,795 A | | 10/1999 | McVenes et al. | 607/122 |
| 6,006,122 A | | 12/1999 | Smits | 600/373 |
| 6,006,137 A | | 12/1999 | Williams | 607/119 |
| 6,120,500 A | * | 9/2000 | Bednarek et al. | 606/41 |
| 6,122,522 A | | 9/2000 | Lee | 455/458 |
| 6,192,280 B1 | | 2/2001 | Sommer et al. | 607/122 |
| 6,235,025 B1 | * | 5/2001 | Swartz et al. | 606/45 |
| 6,259,953 B1 | * | 7/2001 | Lucchesi et al. | 607/119 |
| 6,306,106 B1 | * | 10/2001 | Boyle | 600/585 |
| 6,377,856 B1 | * | 4/2002 | Carson | 607/122 |

* cited by examiner

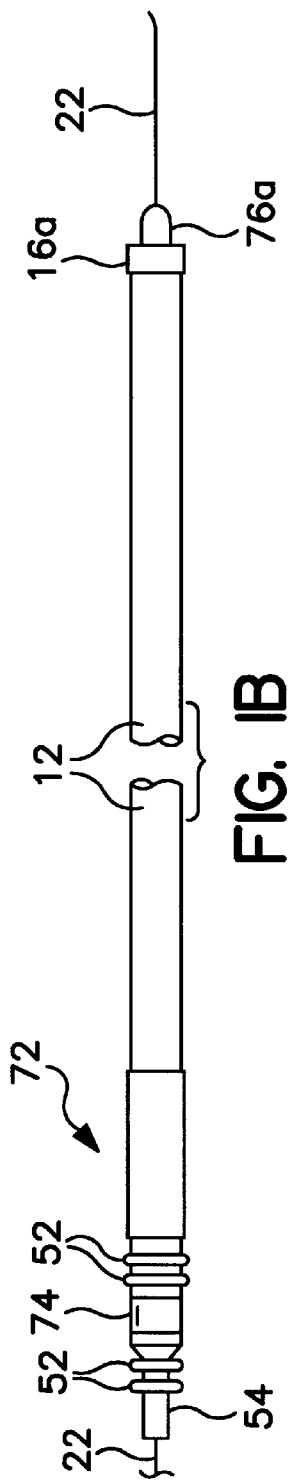
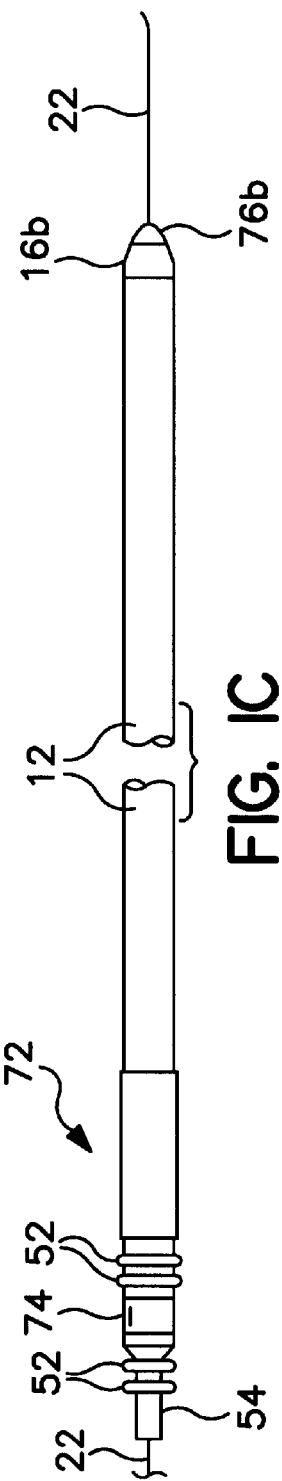
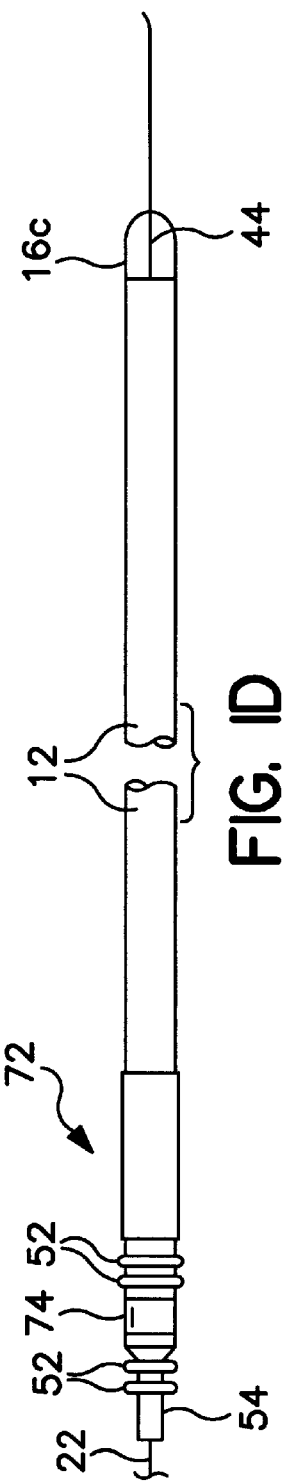
FIG. 1B
FIG. 1C
FIG. 1D

MEDICAL ELECTRICAL LEAD AND METHOD OF USE

RELATED APPLICATIONS

This Application claims priority to provisionally-filed U.S. Patent Application Ser. No. 60/257,025 filed Dec. 20, 2000 entitled "Medical Electrical Lead and Method of Use", which is incorporated herein by reference in its entirety.

The following application includes material that is common to U.S. patent application Ser. No. 09/745,107 filed on Dec. 20, 2000 entitled "Perfusion Lead and Method of Use", which is incorporated herein by reference in its entirety.

The following application further includes material that is common to U.S. patent application Ser. No. 09/324,460 filed Jun. 2, 1999 entitled "Guide wire Placed Implantable Lead with Tip Seal", which is incorporated herein by reference in its entirety.

FIELD OF THE INVENTION

The present invention relates generally to an implantable medical electrical lead; and more particularly, relates to a lead that includes a common port adapted to receive a guiding device, and further adapted to delivery a contrast medium.

BACKGROUND OF THE INVENTION

Implantable medical electrical stimulation and/or sensing leads are well known in the fields of cardiac stimulation and monitoring, including cardiac pacing and cardioversion/defibrillation. In the field of cardiac stimulation and monitoring, endocardial leads are placed through a transvenous route to locate one or more sensing and/or stimulation electrodes along or at the distal end of the lead in a desired location within a heart chamber or interconnecting vasculature. In order to achieve reliable sensing of the cardiac electrogram and/or to apply stimulation that effectively paces or cardioverts the heart chamber, it is necessary to accurately position the electrode surface against the endocardium or within the myocardium at the desired site and fix it during an acute post-operative phase until fibrous tissue growth occurs.

The pacemaker or defibrillator implantable pulse generator (IPG) or the monitor is typically coupled to the heart through one or more of such endocardial leads. The proximal end of such a lead is typically formed with a connector that connects to a terminal of the IPG or monitor. The lead body typically comprises one or more insulated conductive wires surrounded by an insulating outer sleeve. Each conductive wire couples a proximal lead connector element with a distal stimulation and/or sensing electrode. An endocardial cardiac lead having a single stimulation and/or sensing electrode at the lead distal end and a single conductive wire is referred to as a unipolar lead. An endocardial cardiac lead having two or more stimulation and/or sensing electrodes at the lead distal end and two or more conductive wires is referred to as a bipolar lead or a multi-polar lead, respectively.

In order to implant an endocardial lead within a heart chamber, a transvenous approach is utilized wherein the lead is inserted into and passed through the subclavian, jugular, or cephalic vein and through the superior vena cava into the right atrium or ventricle. An active or passive fixation mechanism is incorporated into the distal end of the endocardial lead and deployed to maintain the distal end electrode in contact with the endocardium position.

More recently, endocardial pacing and cardioversion/defibrillation leads have been developed that are adapted to be advanced into the coronary sinus and coronary veins branching there from in order to locate the distal electrode(s) adjacent to the left ventricle or the left atrium. The distal end of such coronary sinus leads is advanced through the superior vena cava, the right atrium, the valve of the coronary sinus, the coronary sinus, and may further be advanced into a coronary vein communicating with the coronary sinus, such as the great vein. Typically, coronary sinus leads do not employ any fixation mechanism and instead rely on the close confinement within these vessels to maintain each electrode at a desired site.

Routing an endocardial lead along a desired path to implant the electrode or electrodes in a desired implantation site, either in a chamber of the heart or in the selected cardiac vein or coronary artery, can be difficult. This is particularly true for steering leads through the coronary sinus and into a branching vein on the left myocardium. Anomalies in the vascular anatomy and the number of branch veins associated with the anatomy make locating the desired path challenging.

Several common approaches have been developed to place electrodes at a desired implant site, such as within the left side of the heart. According to one approach, a guide catheter is steered into the desired location in the vasculature. A lead is then fed through the inner lumen of the catheter such that the lead electrode(s) are positioned at predetermined locations. The guide catheter may then be withdrawn. This type of approach is described in commonly assigned U.S. Pat. Nos. 6,006,137, 5,246,014, and 5,851,226 incorporated herein by reference. The described systems employ highly flexible, catheters surrounding the lead body.

When using a guide catheter, it may be difficult to locate a desired implant site within the torturous curves of the venous system. This is particularly true if the implant site is located within the coronary sinus or one of the branch veins. To aid in locating the desired implant site, radiopaque dye may be injected into the venous anatomy so that the coronary veins are visible using a fluoroscopic device. This procedure, sometimes referred to as a "venogram", allows the surgeon to determine the appropriate path to be followed when performing the implant.

Venograms may be performed using a catheter having a lumen for delivering contrast medium such as fluoro-visible dye into a patient's vascular system. A fluoroscopy device may then be used to create a map of the patient's cardiac vasculature so that a pacing or defibrillation electrode may be steered to an implant site. Such a system is described in U.S. Pat. No 6,122,522 to Tockman which describes a guide catheter having a balloon on a distal tip. Prior to the dye-injection procedure, the balloon is inflated to temporarily occlude the backflow of blood through a vessel so that the dye is retained within the vessels long enough to obtain the venogram. After a venogram is taken, the balloon is deflated to allow a guidewire to be passed through a central lumen of the catheter and into the appropriate venous pathway. The guide catheter is then withdrawn from the venous system and a pacing lead is advanced over the guidewire for placement at the implant site.

One disadvantage of the system described in the '522 patent is that once the catheter is withdrawn, another venogram can not readily be obtained. Thus, if the surgeon encounters difficulty in placing the lead, the guidewire and lead must be withdrawn, and the catheter re-inserted within the vasculature. This is time consuming and increases the risk of venous perforation.

U.S. Pat. No. 5,755,766 to Chastain discloses a lead having a lumen adapted to receive a guidewire. If desired, the guidewire may be withdrawn from the lumen so that the lumen may be utilized to deliver contrast medium. If it is determined that the lead must be re-positioned, the guidewire must be re-inserted and the process repeated. This both lengthens and complicates the implant procedure.

What is needed, therefore, is a system and method that allows a venogram to be obtained while a lead and guidewire is still in place within the vasculature. Ideally, the lead is adapted and sized to allow for placement and use within coronary arteries and cardiac veins such as the veins in the left-side of the heart, including the coronary sinus and branch veins associated with the coronary sinus.

SUMMARY OF THE INVENTION

A medical electrical lead is disclosed having an inner lumen adapted to receive a stiffening member, and which is further adapted to deliver fluoro-visible media while the stiffening member is located within the inner lumen. According to one aspect of the invention, the stiffening member is a guide wire having an inner lumen. The lumen of the guide wire is used to deliver the contrast medium while the guide wire is in place within the lumen of the lead. Delivery of the contrast medium may also occur while the distal tip of the guide wire is advanced past the distal tip of the lead, or while the guide wire remains retracted within the lumen of the lead. In another embodiment, a stiffening member that is sized to occupy only a portion of the lumen of the lead is utilized, with the non-occupied portion of the lumen being large enough to deliver fluoro-visible medium from an injection port at the proximal end of the lead to a delivery port at the distal end of the lead.

The lumen of the lead and/or any inner lumen of the stiffening member may be coated with an anti-inflammatory agent to prevent infection due to bodily fluids contacting the lumen(s). Alternatively, these lumens may be coated partially, or entirely, with a lubricious material that both facilitates the injection of the viscous dye medium, and also allows the stiffening member to be advanced more readily within the lead body.

In one embodiment, the lead includes a sealable member located at the distal end of the lumen of the lead to prevent the ingress of bodily fluids within this lumen. The sealable member includes an opening to allow the stiffening member to be advanced outside of the lead lumen. In one embodiment, the sealable member is a flexible membrane including at least one opening to allow for passage of the stiffening member. In another embodiment, the sealable member includes multiple flap-like structures that seal around a stiffening member advanced distally of the lead body. The flap-like structures may overlap when in the closed position, and may be constructed with a preferential bending direction so that they tend to open distal to the lead body.

In another embodiment, sealable member is a cup-shaped seal element located distal to an electrode, and having a pre-pierced opening to define a path for passage of the guide wire. The seal element is adapted to allow for radial expansion of the seal during passage of the guide wire, while still ensuring that the electrode makes contact with body tissue. In yet another embodiment, the seal element is located within the electrode rather than extending distally of it. The electrode of this configuration is provided with diametrically opposed openings to allow the electrode to spread during passage of a guide wire therethrough.

The lead of the current invention may be placed using a guide catheter as is known in the art. In one embodiment of the invention, the guide catheter includes an inflatable member that may be inflated to at least partially occlude a vessel prior to the delivery of the contrast medium within the vessel. This prevents the contrast media from being flushed from the vessel before a venogram may be obtained. In another embodiment, the lead of the current invention includes an inflatable member and an inflation lumen in fluid communication with the inflatable member. The inflatable member may be inflated prior to delivery of the contrast media.

Other aspects of the current invention will become apparent to those skilled in the art from the following detailed description, and the accompanying figures.

BRIEF DESCRIPTION OF THE DRAWINGS

FIG. 1B illustrates a second embodiment of a lead according to the present invention.

FIG. 1C illustrates yet another alternative embodiment of the lead according to the present invention.

FIG. 1D is a plan view of a fourth embodiment of a lead according to the present invention.

DETAILED DESCRIPTION OF THE DRAWINGS

Figure 1A:
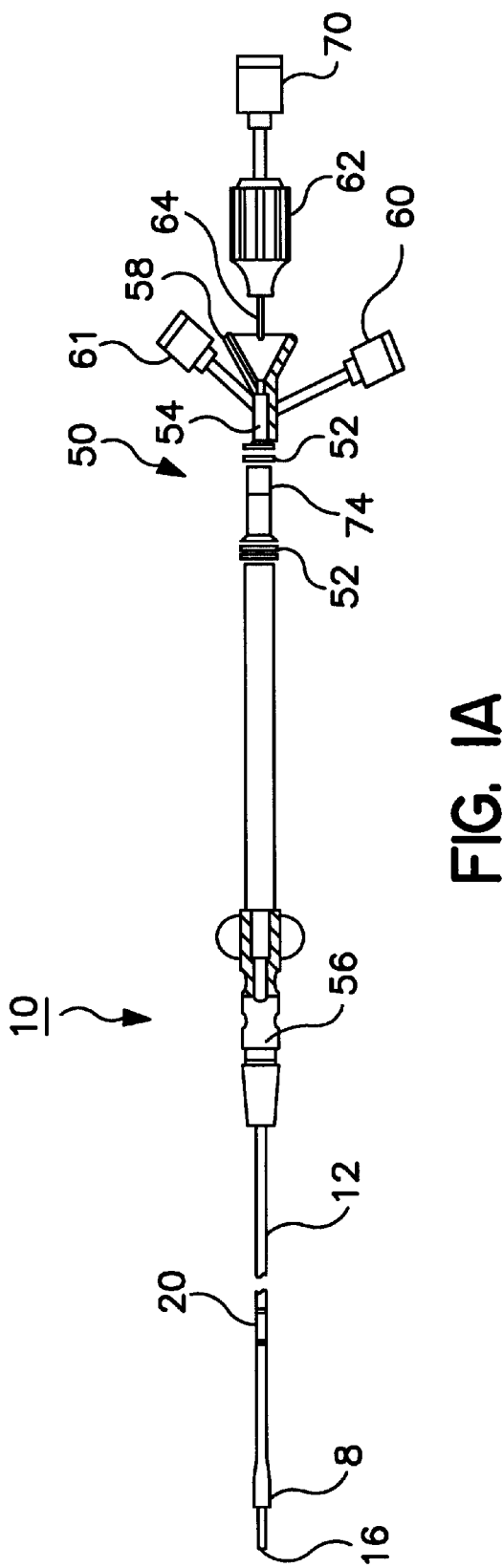
FIG. 1A is a plan view of one embodiment of a lead that may be used in accordance with the current invention.

FIG. 1A is a plan view of one embodiment of a lead that may be used in accordance with the current invention. Lead 10 comprises an elongate lead body 12 and a tip electrode assembly 16 disposed at the distal section of lead body 12. Tip electrode assembly 16 includes a port (not shown in FIG. 1) that is in fluid communication with a lumen within the lead body for the delivery of dye.

Distal section of lead body may further include a ring electrode 20, although in one embodiment, the lead is a unipolar, single-electrode lead. Lead body 12 is covered by an insulative sleeve of flexible biocompatible and biostable insulating material, such as polyurethane or silicone rubber. At the proximal end of lead 10, a terminal assembly designated generally as 50 is provided for coupling lead 10 to an implantable pulse generator (not shown). Terminal assembly 50 is provided with sealing rings 52 and a connector pin 54, all of a type known in the art. A connector ring 74 is provided to couple to electrode 20. An anchoring sleeve 56 may also be provided on lead body 12. As would be familiar to those of ordinary skill in the art, anchoring sleeve 56 slides over lead body 12 and serves as a point for suturing lead body 12 to body tissue at the insertion point of lead 10 in a fashion known in the art. Anchoring sleeve 56 and terminal assembly 50 are preferably fabricated from silicone rubber, although they may also be constructed of any other suitable biocompatible material known in the art.

Lead 10 as shown in FIG. 1 may also include an adapter 58 for coupling to connector pin 54. Adapter may include one or more side arm sealing ports 60 and 61, as will be discussed further below. Adapter 58 may further serve as a stylet guide for stylet assembly 62 that is required to impart stiffness to lead 10 during the implantation procedure. Stylet assembly includes a stylet body 64 that is received within an inner lumen (not shown in FIG. 1) of the lead shown in FIG. 1 as a stiffening member to aid in lead placement. Adapter 58 and stylet assembly 62 are discarded after use and before connection of connector pin 54 to a pacemaker pulse generator. Alternatively, a guide wire may be used instead of the stylet assembly to impart stiffness to the lead body. Stylet assembly 62 is shown coupled to a sealing port 70 which may be used to inject fluid into an inner lumen of a stylet or hollow guide wire in a manner to be discussed below.

Other lead body types may be substituted within the context of the present invention, including lead bodies employing multiple lumen tubes and/or stranded or braided conductors as disclosed in U.S. Pat. No. 5,584,873 issued to Shoberg et al, and incorporated herein by reference in its entirety. Alternatively, the lead may include additional conductors arranged either within a multi-lumen lead body or concentrically, as disclosed in U.S. Pat. No. 4,355,646 issued to Kallok et al and incorporated herein by reference in its entirety. Additional pacing electrodes, sensors, or defibrillation electrodes, may of course be added to the lead body and coupled to additional conductors.

FIG. 1B illustrates a second embodiment of a lead according to the present invention. Elements of FIG. 1B that correspond to like structures of FIG. 1A are designated with the same numerals. At the proximal end of the lead body is a connector assembly 72 which takes the form of an IS-1 connector assembly conventionally used in commercially available cardiac pacing leads. The connector assembly includes a conductive connector pin 54 which is coupled by means of the conductor within lead body 10 to a tip electrode 16a in the manner discussed above with respect to FIG. 1A. A connector ring 74 is also provided, which in this embodiment is not coupled to any electrode, but which in the context of leads employing additional electrodes would be coupled to a second conductor within lead body 12. Sealing rings 52 are provided to prevent fluid entry into the connector block into which the lead is inserted.

The embodiment of FIG. 1B includes a guide wire 22 shown exiting the proximal end of the lead through connector pin 54 and exiting the distal end of the lead through a seal member 76a. The configuration and operation of electrode 16 and seal member 76 are discussed in more detail below.

FIG. 1C illustrates yet another alternative embodiment of the lead according to the present invention. This configuration includes a slightly different configuration for electrode, shown as electrode 16b and seal member 76b.

FIG. 1D is a plan view of a fourth embodiment of a lead according to the present invention. In this embodiment, the electrode 16c contains the seal member 76c (not visible in this view). It can also be seen in this view that the electrode 16c is provided with a longitudinal slot 44 which, as discussed below, allows for expansion of the electrode 16c during passage of the seal through the internal seal member 76c.

Figure 2:
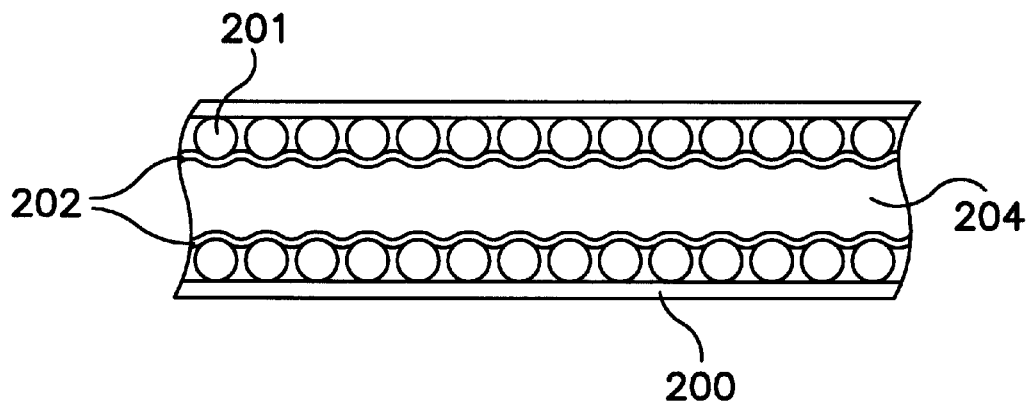
FIG. 2 is an exploded, side cutaway view of distal section of lead body according to one embodiment of the current invention.

FIG. 2 is an exploded, side cutaway view of the distal section of lead body according to one embodiment of the current invention. Lead includes an insulative outer jacket that may be formed of silicone, a polymer such as polyurethane or polytetrafluoroethylene (PTFE), or any type of suitable biocompatible, biostable material. A helical wound coil 201 is provided to couple to tip electrode assembly 16. The coil may be formed of any type of conductive material known in the art. A coating 202 that may consist of an anti-inflammatory agent such as silver nitrate may be applied to the coil to prevent infection from being promoted by the open-lumen system of the current invention. This coating could be applied using a vapor deposition method, as known in the art. Alternatively, a lubricious coating may be applied to the inner lumen of coil 201 or to the entire coil using materials such as Teflon or ETFE. This coating is adapted to allow the guide wire or stylet to slide more readily within the lumen. Another lubricious material that may be used for this purpose is polyetheretherketone (PEEK) polymer (VICTREX® 381G or VICTREX® 450 manufactured by Victrex PLC).

Coil 201 defines an inner lumen 204 that is used both for dye delivery and for receiving a stiffening member such as a guide wire or a stylet in a manner to be discussed further below.

Figure 3:
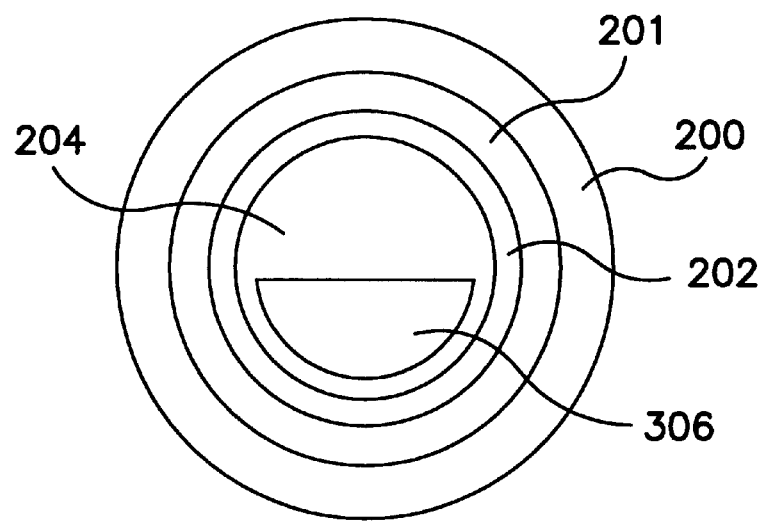
FIG. 3 is a cross-sectional view of one embodiment of the lead including a guide wire inserted into lead lumen.

FIG. 3 is a cross-sectional view of one embodiment of the lead, and further shows a first embodiment of a guide wire 306 inserted into lumen 204 of lead 10. In the embodiment shown in FIG. 3, guide wire 306 has a cross-sectional shape that is semi-circular to allow approximately half of the lumen 204 to remain open when the guide wire is in place within the lead. This allows dye to be injected through lumen 204 via a syringe inserted into side arm 60 so that a venogram may be taken during lead placement.

Figure 4:
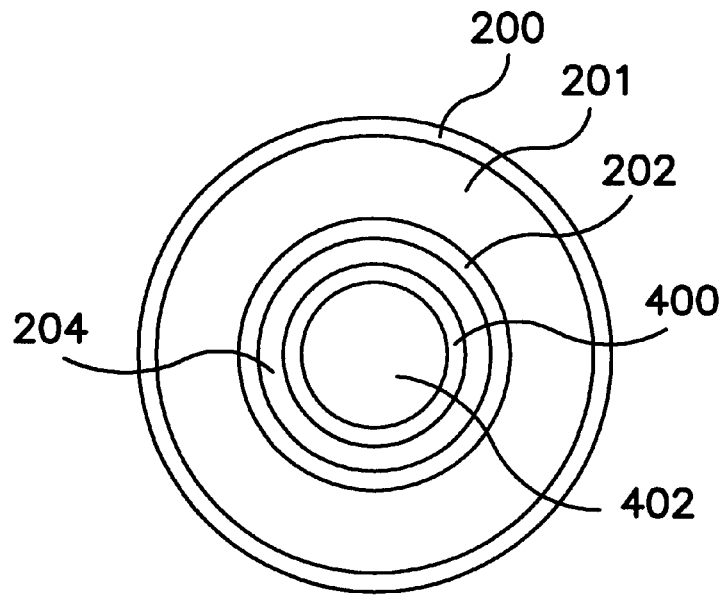
FIG. 4 is a cross-sectional view of an alternative embodiment of the lead, including another embodiment of a guide wire inserted into lumen the of lead.

FIG. 4 is a cross-sectional view of an alternative embodiment of lead 10, and further shows another embodiment of a guide wire 400 inserted into lumen 204 of the lead. In this embodiment, guide wire 400 is a hollow, tubular member such as may be formed of a helically-wound spring coil described in commonly-assigned U.S. Pat. No. 4,815,478 to Buchbinder et al., incorporated herein by reference in its entirety.

A lumen 402 is defined by the hollow, tubular member of guide wire 400 such that a syringe inserted into seal port 70 of FIG. 1 delivers dye to the lumen. This allows a venogram to be taken while the stylet is in place within the lumen. The entire tubular member, or alternatively, just the inner lumen, may be coated with a lubricious material such as Teflon, ETFE, or PEEK to aid in the delivery of the viscous dye through the lumen. Coating of the exterior surface of tubular member may rther be beneficial in aiding the advancement of the guide wire through lumen 204.

Figure 5:
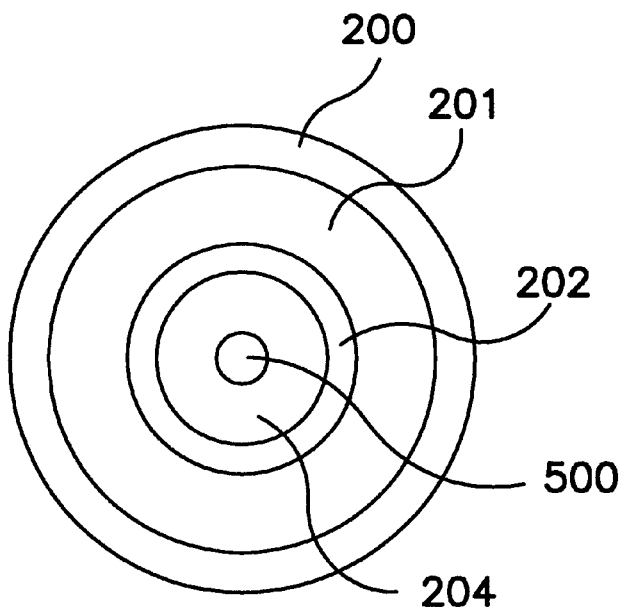
FIG. 5 is a cross-sectional view of yet another embodiment of the lead, and further shows yet another embodiment of a guide wire.

FIG. 5 is a cross-sectional view of yet another embodiment of the lead, and further shows yet another embodiment of a guide wire inserted into lumen 204. In this embodiment, guide wire 500 is a solid structure with a diameter that is considerably smaller than the diameter of lumen 204. In one embodiment, the outer diameter of guide wire 500 is sized to be less than half of the inner diameter defined by coating 202. A syringe inserted into seal port 60 of FIG. 1 delivers dye into the lumen around the stylet when the stylet is in place.

Figure 6:
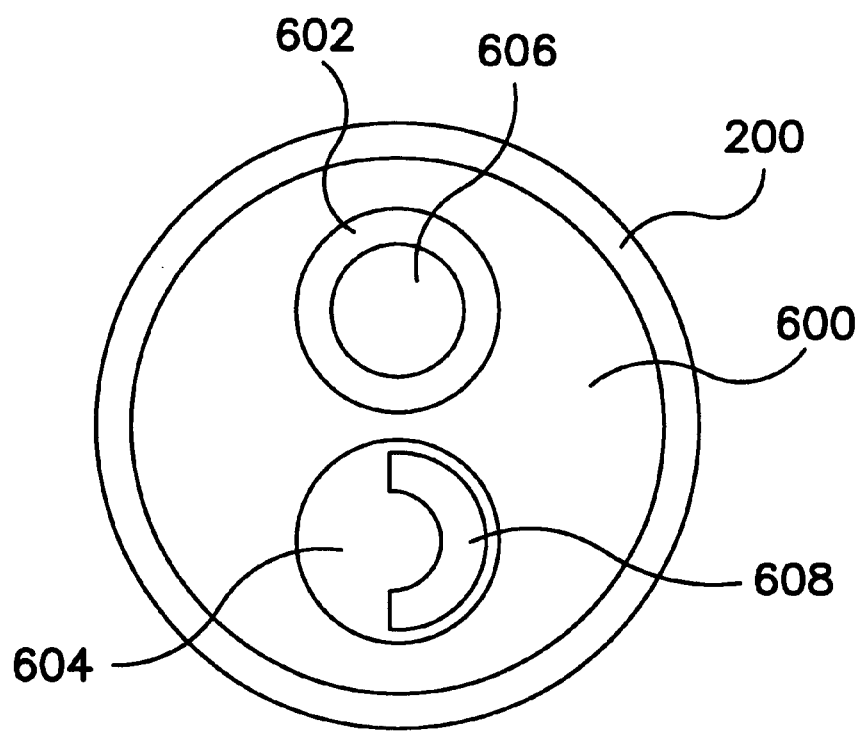
FIG. 6 is a cross-sectional view of a fourth embodiment of the lead.

FIG. 6 is a cross-sectional view of a fourth embodiment of the lead. In this embodiment, outer jacket 200 surrounds a tubular member 600 that may be formed of silicone, a polyurethane, or another type of polymer suitable for this purpose and known in the art. In a preferred embodiment, outer jacket 200 is formed of a more stiff polyurethane, whereas tubular member 600 is formed of a relatively flexible silicone. The stiffness of the jacket 200 increases the pushability and the ability to transfer torque down the body of the lead.

Tubular member 600 includes lumens 602 and 604. Lumen 602 houses a conductor 606, which may be a single or multi-filar conductor which couples tip electrode 16 to connector pin 54. Lumen 604 is adapted to receive guide wire 608, which in this embodiment is an open "C" shape to allow passage of dye through the non-occluded portion of the lumen. Dye is injected into lumen 604 via a syringe inserted into seal port 70 of FIG. 1A.

Figure 7:
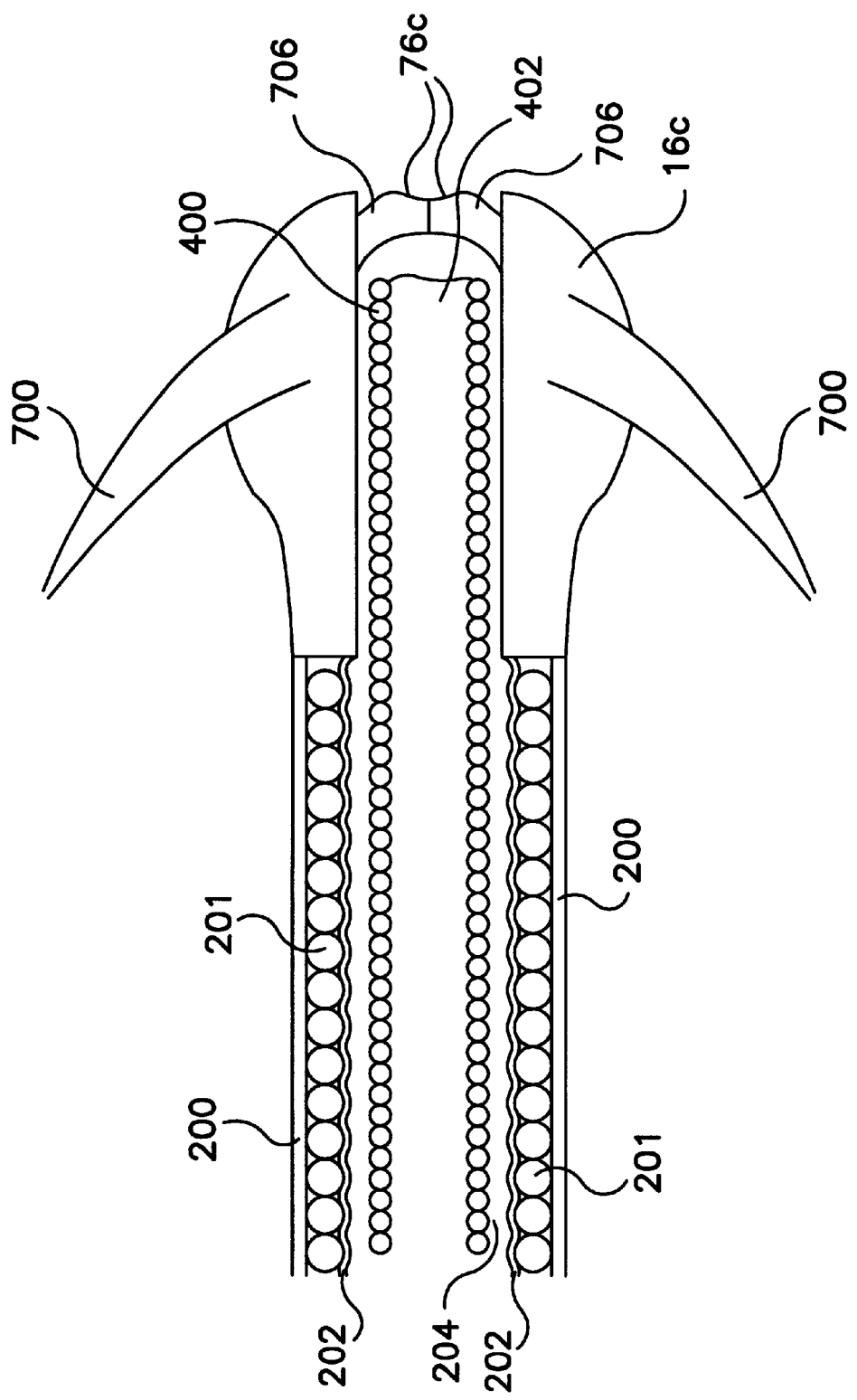
FIG. 7 is a side cutaway view of a guide wire such as shown in FIG. 4 advanced to the distal tip section of the lead.

FIG. 7 is a side cutaway view of a guide wire such as shown in FIG. 4 advanced to the distal tip section 8 of lead 10. Guide wire includes a coil 400 as discussed above in reference to FIG. 4. Coil defines lumen 402 for injecting dye. FIG. 7 further shows the various elements of the lead, as described above in reference to FIG. 2.

The lead of FIG. 7 includes tip electrode 16 of FIG. 1, which is coupled to the connector pin 54 via coil 201. Tip electrode 16 may be any of the various types of pacing electrodes known in the art such as a porous platinized electrode assembly. Alternatively, it could be a steroid-eluting porous pacing electrode, as described in U.S. Pat. No. 4,506,680 to Stokes, and related U.S. Pat. Nos. 4,577, 642; 4,606,118; and 4,711,251, all commonly assigned to the assignee of the present invention and incorporated by reference herein in their respective entireties. The electrode disclosed in the Stokes '680 patent is constructed of porous, sintered platinum, titanium, or the like, for example.

Electrode 16 is shown in this embodiment to include tines 700. Such pliant tines or barbs are known in the art as a passive fixation mechanism for securing the electrode at the desired location of implant by engaging the trabeculae within the heart chamber. As an alternative, an "active" fixation mechanism may be used, including corkscrews, hooks, piercing barbs or other anchoring structures arranged at, or near, the distal tip for penetration of cardiac tissue upon proper positioning of the electrode. Yet other mechanisms are available for securing leads placed within cardiac veins such as the coronary sinus. Fixation devices of this nature are disclosed in U.S. Pat. Nos. 5,964,795, 6,006,122, and 5,387,233 which are incorporated herein by reference.

As discussed above with respect to FIGS. 1B through 1D, the lead of the current invention may further include a port having a sealable member 76. This port may be included in electrode 16c of FIG. 1D and FIG. 7. This port prevents blood from entering the lumen of the lead body through the opening at the distal end of the lead. Normally, sealable member 76c is in the closed position to prevent fluids, including blood, from entering lumen 204. However, the distal tip of guide wire 400 may be advanced through the sealable member so that dye may be injected into the vessel to obtain a venogram. Alternatively, the sealable member may be opened by injecting dye through lumen 402 of guide wire which remains retracted with lumen 204 of lead 10. The pressure resulting from this dye injection exerts a force on the proximal side of sealable member that is much greater than the pressure exerted by body fluids on the distal side of sealable member 76c. This causes sealable member to open, releasing the dye into the body.

In one embodiment, sealable member may be hinged to have a preferential direction of movement such that the sealable member tends to open outward towards the distal end of the lead. Alternatively, this preferential direction of movement may be provided by slits, or cutaway portions 706, of the sealable member positioned to weaken the distal side of the sealable member, allowing it to open more easily in the distal direction.

Figure 8:
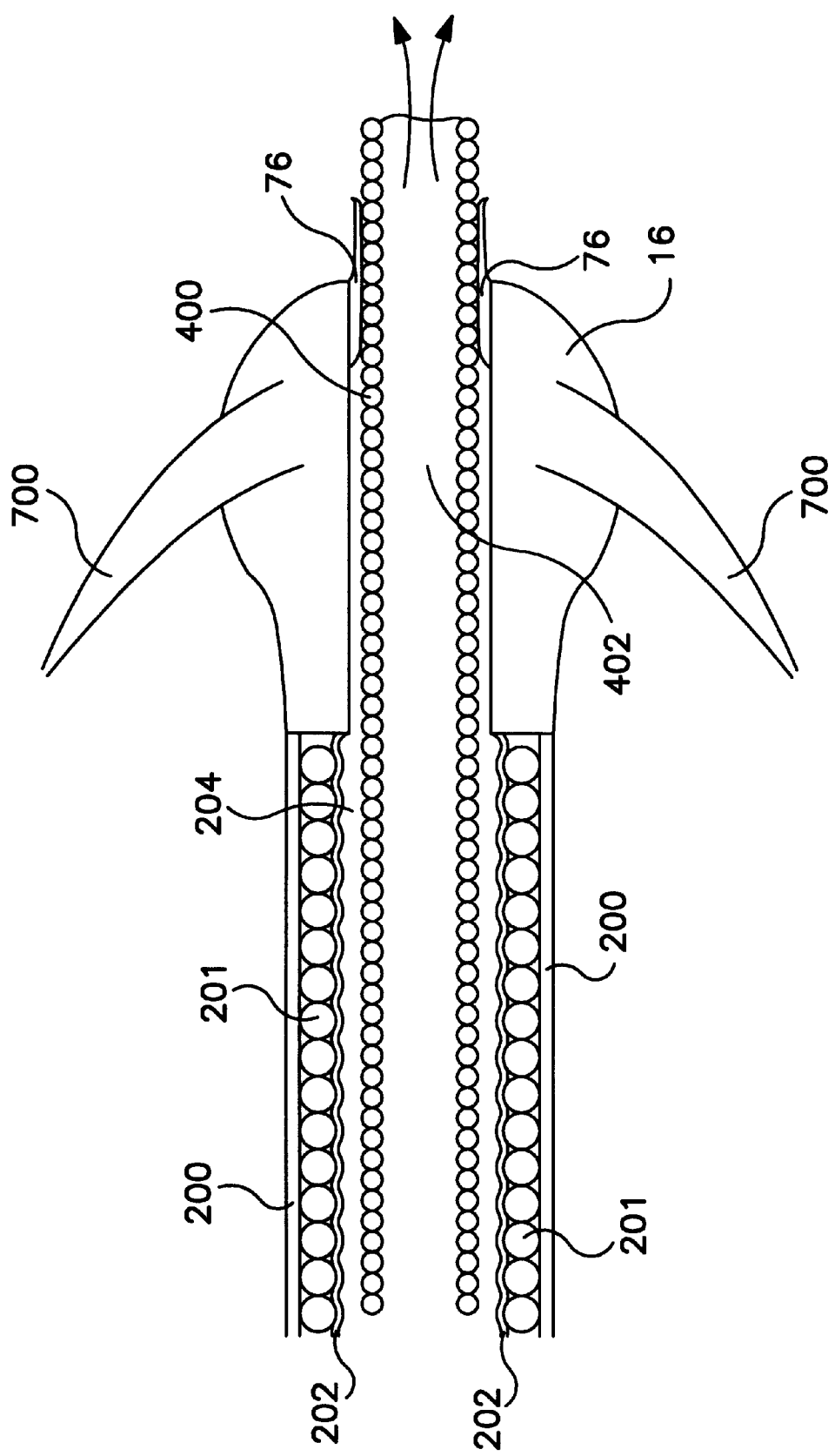
FIG. 8 is a side cutaway view showing the distal end of the guide wire extending beyond the distal end of the lead to deliver dye to a surrounding vessel.

FIG. 8 is a side cutaway view showing the distal end of guide wire 400 extending beyond the distal end of the lead to deliver dye to a surrounding vessel. The flaps of sealable member 76 are shown pushed open by the outer surface of guide wire 400. The flaps are made of resilient material that resumes the original closed position when guide wire 400 is again retracted within lumen 204.

Figure 9:
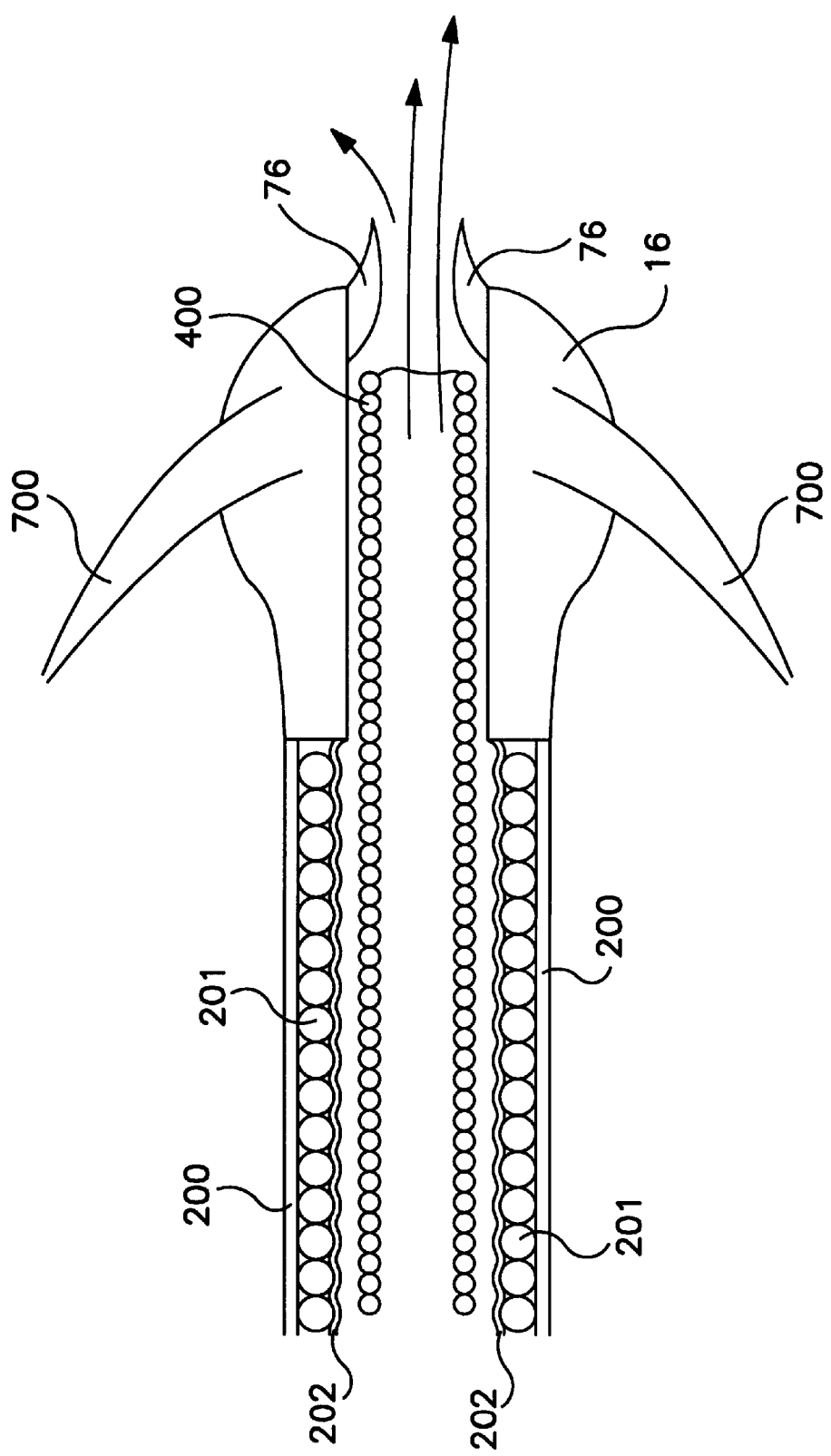
FIG. 9 is a side cutaway view illustrating the manner in which sealable member may be opened by the pressure differential between the proximal and distal sides of sealable member while the guide wire remains retracted within the lead lumen.

FIG. 9 is a side cutaway view illustrating the manner in which sealable member may be opened by the pressure differential between the proximal and distal sides of sealable member while guide wire 40 remains retracted within lumen 204.

According to one embodiment of the invention, sealable member is a pierceable silicone rubber membrane. This member may include one or more slits to allow the guide wire to be inserted therethrough. In another embodiment, sealable member includes two flaps that overlap.

Figure 10B:
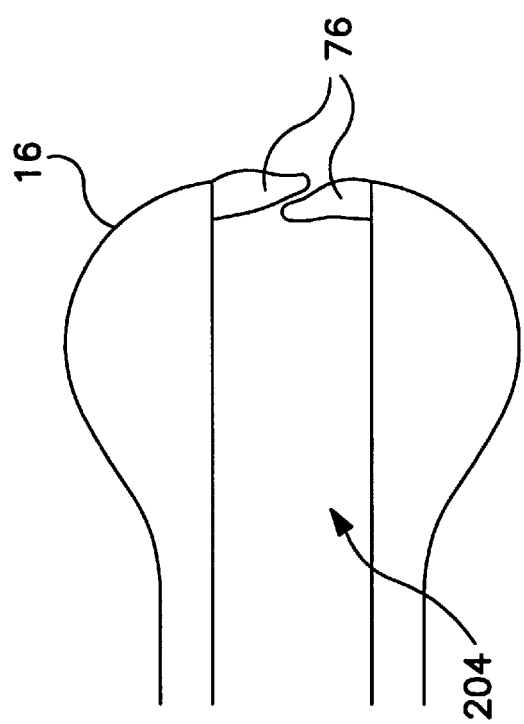
FIG. 10B is a side cutaway view showing yet another embodiment of sealable member, wherein two flap-like structures are adapted to overlap when in the closed state.
Figure 10A:
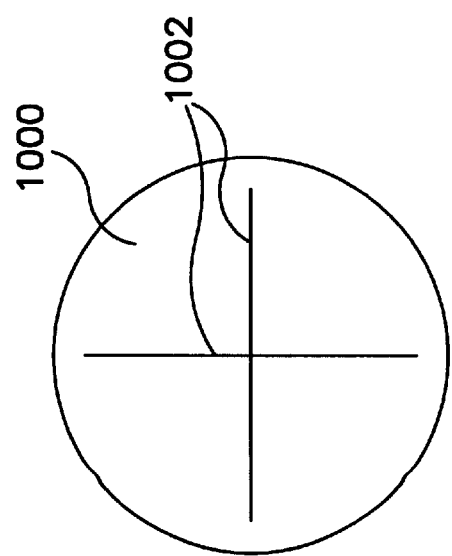
FIG. 10A is a cross-sectional end view showing a membrane including slits to allow for insertion of the guide wire.

FIG. 10A is a cross-sectional end view showing a membrane 1000 including slits 1002 to allow for insertion of the guide wire. In FIG. 10A, the slits are shown in the closed position. When a guide wire is inserted through slits, the flaps of the member 1000 close around the outer diameter of the guide wire to prevent ingress of fluids. Member 1000 may be formed of a flexible silicone membrane, for example.

FIG. 10B is a side cutaway view showing yet another embodiment of sealable member 76, wherein two flap-like structures are adapted to overlap when in the closed state. Opening of these flaps may be accomplished by applying pressure from a guide wire or stylet distal tip, or by a pressure differential created by the injection of dye into lumen 204, or the lumen of a guide wire or stylet.

Other embodiments of the seal members 76a and 76b as shown in FIGS. 1B and 1C are described further in the following paragraphs. Similar seal members are described in U.S. patent application Ser. No. 09/324,460 filed Jun. 2, 1999, which is incorporated herein by reference in its entirety.

Figure 11:
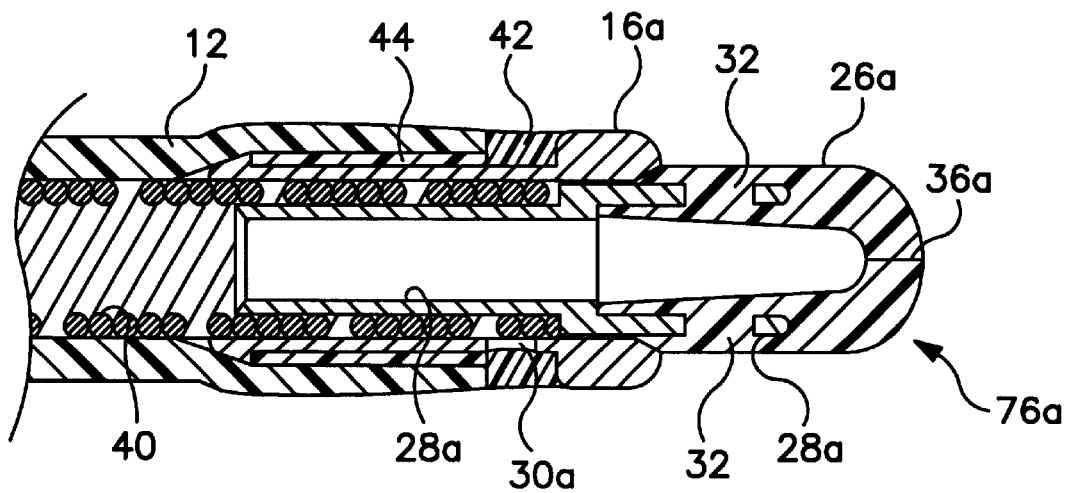
FIG. 11 is a sectional view through the distal portion of the lead of FIG. 1B, and illustrates yet another embodiment of seal member.

FIG. 11 is a sectional view through the distal portion of the lead of FIG. 1B, and illustrates yet another embodiment of seal member 76. In this view it can be seen that the electrode 16a is coupled to a coiled conductor 40 (similar to coil 201 of FIG. 2) by means of an internal conductive sleeve 28a. Electrode 16a may be crimped to compress conductor 40 between internal conductive sleeve 28a and electrode 16a. Visual verification that conductor 40 is properly located prior to crimping is facilitated by bore 30a. The distal portion of inner sleeve 28a is provided with two bores 32. By molding the cup-shaped seal element 26a of seal member 76 to the distal portion of inner sleeve 28a, the bores 32 provide for a mechanical interlock of the seal and the sleeve. As illustrated at 36a, the cup-shaped seal element 26a is pre-pierced to define a path for the guide wire to pass through the seal.

The extension of the cup-shaped distal portion of seal element 26a past the distal end of the sleeve 28a to which it is attached allows for radial expansion of the seal during passage of the guide wire. Seal element 26a and electrode 16a are preferably configured so that the expanded diameter of the seal element 26a during passage of the guide wire is still less than the outer diameter of the electrode 16a, so that the electrode 16a may still make contact with the heart, particularly in those circumstances in which the lead is employed as a coronary sinus lead. For example, in the embodiment illustrated, the diameter of seal element 26a in its relaxed position as illustrated is approximately 0.050 inches, and the diameter of electrode 16a is approximately 0.072 inches. With a 0.018 inch guide wire passed through seal element 26a, the expanded diameter of seal element 26a is approximately 0.068 inches, allowing electrode 16a to make contact laterally, for example with the wall of the coronary sinus, even while the guide wire is present. The proximal exposed edge of electrode 16a is radiused and extends slightly laterally outward (e.g. 0.002") of insulative lead body 12, in order to further facilitate lateral contact of the electrode with body tissue, particularly in cases in which the lead is used in the patient's coronary sinus. The lead is optionally provided with a ring-shaped monolithic controlled release device 42, mounted around the electrode 16a. Controlled release device 42 preferably elutes an anti-inflammatory agent such as sodium dexamethasone phosphate, and may be fabricated as described in U.S. Pat. No. 4,972,848, issued to DiDomenico, et al., incorporated herein by reference in its entirety. A plastic band 44 is mounted around electrode 16a and lead body 12 is adhesively bonded to the plastic band, coupling lead body 12 to the electrode.

Figure 12:
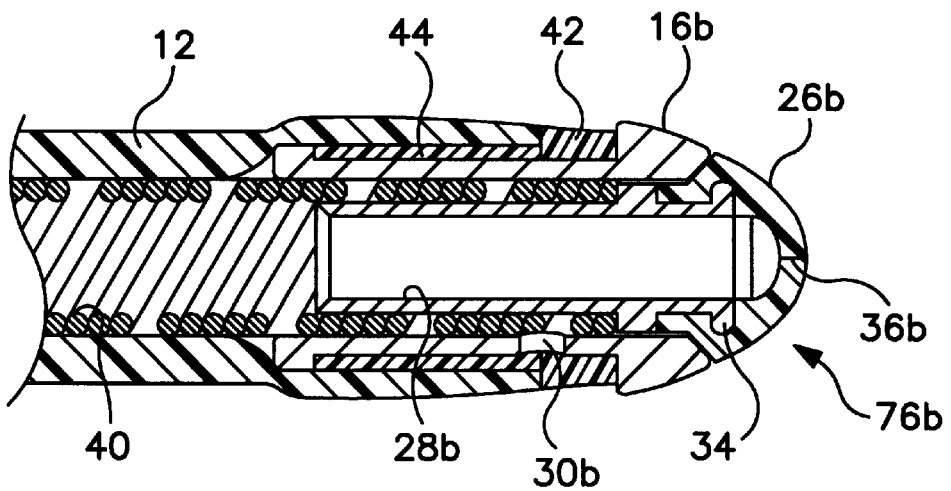
FIG. 12 illustrates a sectional view through the distal portion of the lead illustrated in FIG. 11B.

FIG. 12 illustrates a sectional view through the distal portion of the lead illustrated in FIG. 1C. Identically labeled components correspond to those in FIG. 11. In this case, the electrode 16b is similarly provided with an internal conductive sleeve 28b, coupled to electrode 16b in the manner discussed in conjunction with FIG. 11. In this case, however, the sleeve 28b is provided with a laterally extending flange or ridge 34, and seal element 26b is retained by means of interaction of the laterally extending ridge 34 and the ring electrode 16b. In this case, the seal and electrode together are configured to provide a smooth rounded contour, without abrupt transitions, facilitating passage of the lead through the vascular system and in particular facilitating passage through the coronary sinus. As in the case of seal element 26a, the distal tip of seal element 26b takes the form of a cup-shaped member, allowing for radial expansion of the sleeve during passage of the guide wire through the sleeve. The sleeve is pre-pierced at 36b to define a path through which the guide wire passes. As in the case of the seal element 26a, one preferred material for fabrication of the seal is silicone rubber.

Figure 13:
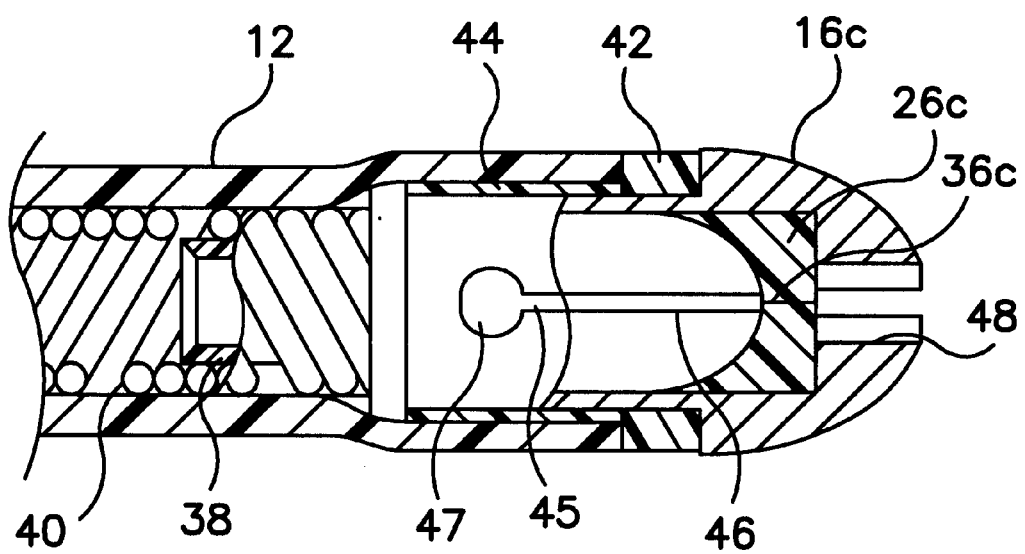
FIG. 13 is a sectional view through the distal portion of the lead of FIG. 1D.

FIG. 13 is a sectional view through the distal portion of the lead of FIG. 1D. Identically numbered components correspond to those illustrated in FIGS. 11 and 12 above. In this embodiment, the seal element 26c is located within the electrode 16c of FIG. 1D, rather than extending distally of it. While normally, location of a seal within the electrode would prevent radial expansion of the seal during passage of the guide wire, electrode 16c is provided with two diametrically opposed longitudinal slots 45 and 46, allowing the distal ends of electrode 16c to spread apart from one another due to outward force exerted by seal element 26c, during passage of a guide wire therethrough. The proximal ends of the slots 45 and 46 are optionally provided with enlarged circular recesses 47 to further facilitate the radial opening of the electrode 16c. The width of slots 45 and 46 is preferably less than the diameter of the guide wire, and is less than the diameter of the distal bore 48, which is slightly larger in diameter than the guide wire to be used with the lead. The configuration of slots 45 and 46 extends properly from the distal end of the electrode, during both advancement of the guide wire through the distal tip of the electrode and movement of the electrode along the guide wire during implantation of the lead. In the embodiment illustrated in FIG. 13, a crimping sleeve 38 is provided and coiled conductor 40 is crimped between sleeve 38 and electrode 16c in order to provide electrical connection thereto. As in the case of the leads illustrated in FIGS. 11 and 12, a preferred material for seal element 26c is silicone rubber, and the seal is preferably pre-pierced at 36c as discussed above in conjunction with the leads of FIGS. 3 and 4.

Figure 14:
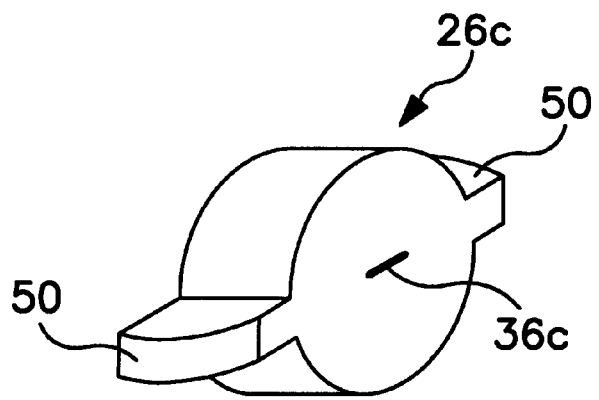
FIG. 14 is a perspective view of seal member.

FIG. 14 illustrates seal member 26c in a perspective view. In this view, it can be seen that seal member 26c is provided with laterally extending ridges 50, which are configured to be located within slots 47 and 45, distal to lead body 12. Ridges 50 prevent fluid ingress into the electrode 16c along portions of the slots distal to the controlled release device 52. The ridges 50 may be adhesively bonded to the controlled release device 52 if necessary, to provide a reliable fluid seal.

Figure 15:
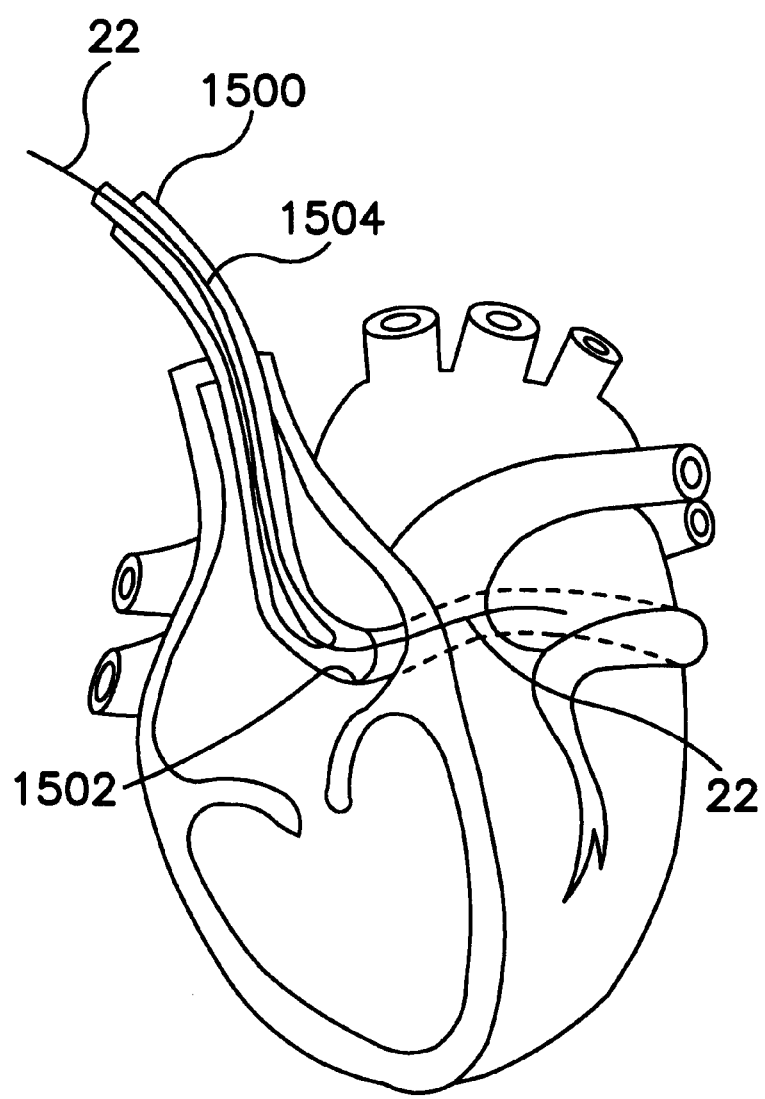
FIG. 15 is a diagram of the inventive lead implanted within a heart.

During use, lead 10 may be inserted into the vasculature using a guide catheter, as is known in the art, and as shown in FIG. 15.

FIG. 15 is a schematic diagram of the lead 10 according to the present invention, which may correspond to any of the leads illustrated in FIGS. 1A through 1D, or other embodiments of the present invention, passing through a guide catheter 1500 and carrying a guide wire 22 extending through the entire length of the lead and out its distal end. As illustrated, the distal end 1502 of guide catheter 1500 is placed adjacent the opening of the coronary sinus and guide wire 22 extends into the coronary sinus. During implantation of the lead, the tip of guide wire 22 is advanced to a desired location within the patient's vascular system, for example the coronary sinus, and the lead 1504 is passed along the guide wire 22 until it reaches its desired location. Use of a guide catheter 1500 to facilitate advancement of the guide wire and/or the lead to a position adjacent its desired ultimate location, for example the ostium of the coronary sinus, is optional. After the lead is placed in its desired location, the guide wire 22 and the guide catheter 1500 (if provided) are removed.

As discussed above, when using a guide catheter, it may be difficult to locate a desired implant site within the torturous curves of the venous system. To aid in locating the desired implant site, radiopaque dye may be injected into the venous anatomy using the hollow guide wire or stylet of the current invention, or by injecting dye directly into lumen 204 of lead 10 with, or without, the guide wire or stylet being located within lumen 204.

To ensure that the dye is retained in the vasculature long enough to obtain the venogram, an inflatable balloon located on the distal tip of a guide catheter may be inflated to temporarily occlude the vessel. This prevents the backflow of blood from flushing the dye as it is dispersed from the tip of the lead. After balloon inflation, the radiopaque dye may then be injected through lumen 204, or through the lumen 402 of the hollow guide wire or stylet. The balloon may then be deflated to allow blood flow to resume. Such a system is described in U.S. Pat. No. 6,122,522 to Tockman which describes a guide catheter having a balloon on a distal tip. In one embodiment, it may be desirable to incorporate a balloon on the distal end of lead body 10. A lead of this nature is described in co-pending U.S. application Ser. No. 09/745,107 filed on Dec. 20, 2000 entitled "Perfusion Lead and Method of Use", which is incorporated herein by reference in its entirety.

Figure 16:
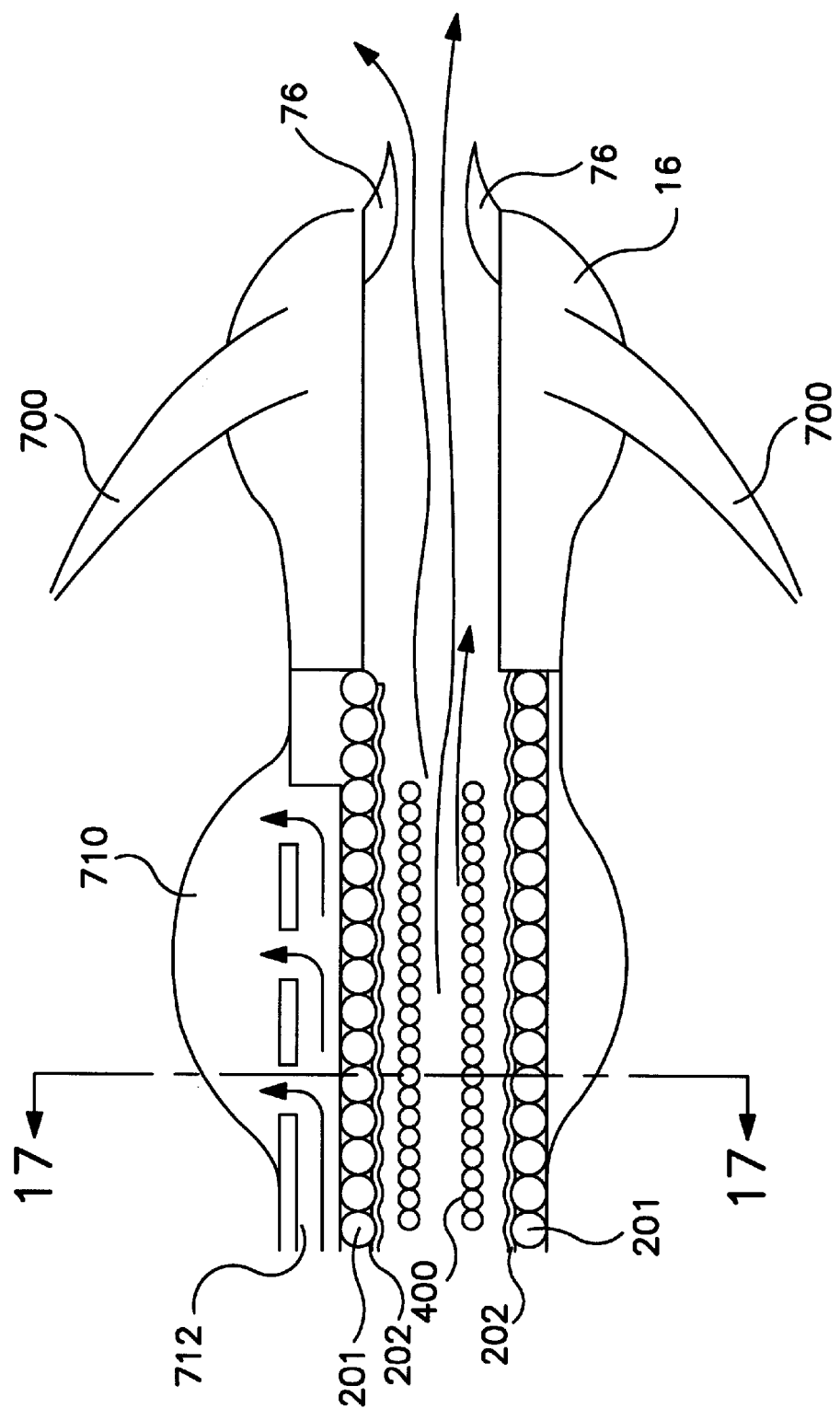
FIG. 16 is a plan view of another embodiment of the lead with a balloon positioned distal to the electrode.

FIG. 16 is a plan view of another embodiment of lead 10 with balloon 710 positioned distal to electrode 16. Proximal to the tip electrode assembly 16 is a balloon 710. The balloon 710 may be formed of compliant or non-compliant polymer materials. Example of materials that are suitable for balloon construction include polyethelene, nylon, PET, and laytex. In one embodiment, the balloon 710 is formed of polyurethane (Pellathane) having a stiffness of approximately 80A Shore which is available from World Medical of Miami, Fla. In yet another embodiment, the balloon 710 may be constructed of a material that is permeable, or that has micro-pores to allow the fluid from within the balloon 710 to slowly seep to the balloon exterior. A "weeping" balloon of this type is described in U.S. Pat. No. 5,087,244 to Wolinsky et al. which is incorporated by reference in its entirety. In one embodiment, the balloon 710 has an inflated diameter of between approximately 1.5 to 4 mm, and a length of between approximately 10 to 40 mm. The balloon 710 may be attached to the lead body using a thermal or adhesive, as is known in the art.

Balloon 710 is fluidly coupled to an inflation lumen 712 that extends to side arm 61 (FIG. 1). A syringe inserted in side arm 61 may inject fluid into inflation lumen 712 to inflate balloon 18 to a size that partially, or fully, occludes a vessel in which lead 10 is placed. After the balloon is inflated, dye may be injected via guide wire in the manner discussed above so a venogram may be obtained.

Figure 17:
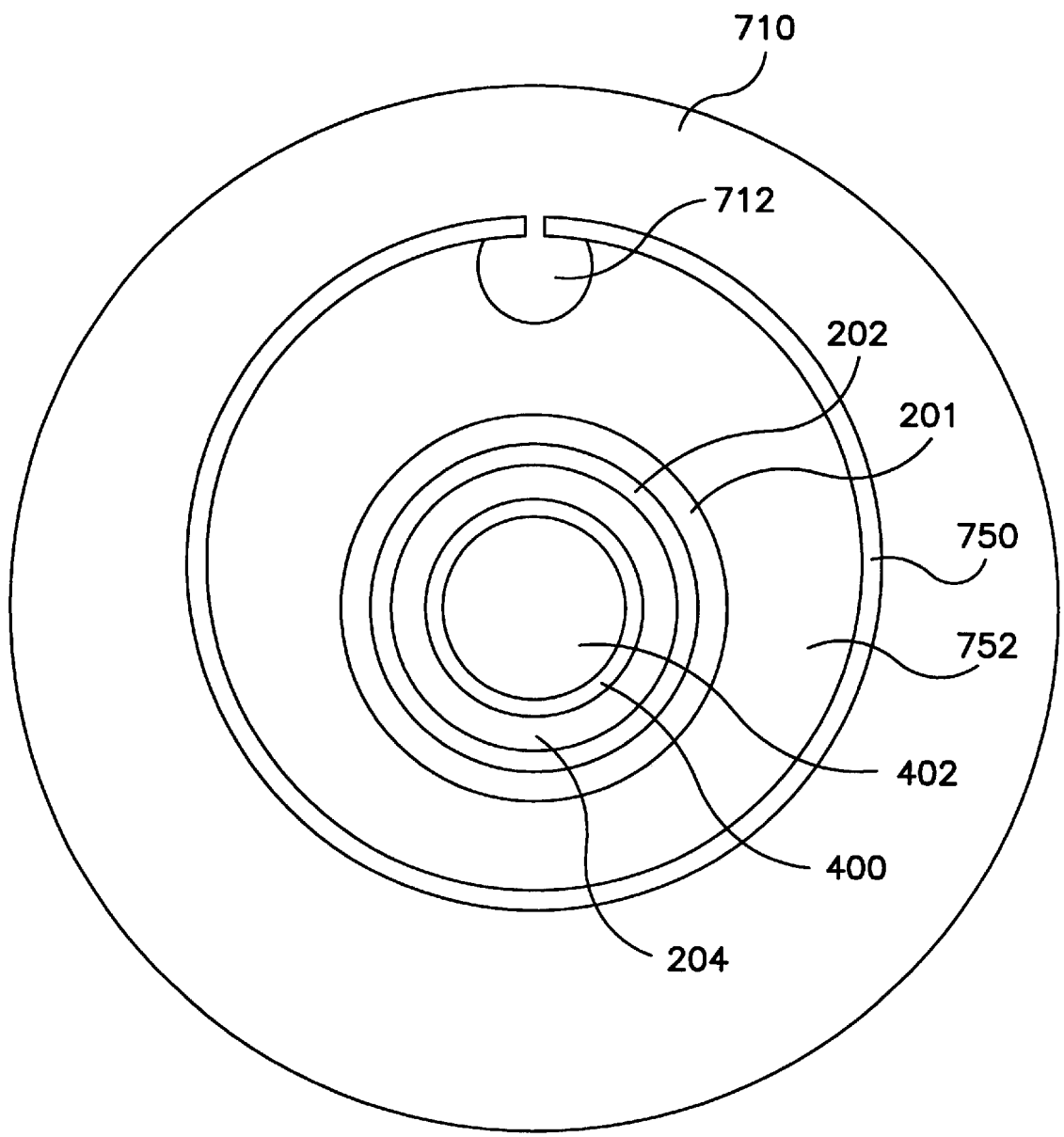
FIG. 17 is a cross-sectional view of the lead of FIG. 16 at line 17—17.

FIG. 17 is a cross-sectional view of the lead of FIG. 16 at line 17—17. Jacket of lead 750, which may be formed of a polymer such as polyurethane, surrounds silicone tube 752, which includes both inflation lumen 712 and coiled conductor 201. Inflation lumen 712 is coupled to balloon 710, shown inflated. Coiled conductor may have a lubricious or anti-inflammatory coating 202 on the inner wall, or alternatively, completely coating the individual coils, as discussed above. Coil 202 defines lumen 204 shown housing guide wire 400. Guide wire 400 is of a hollow, coil structure according to one embodiment discussed above.

Variations and modifications to the present invention may be possible given the above disclosure. However, all such variations and modifications are intended to be within the scope of the invention claimed by this letters patent.

In conjunction with the above disclosure, we claim:

1. An implantable medical device for use in a body, comprising:
    an elongated lead body having a proximal end, a distal end, and a lumen;
    an electrode at the distal end of the lead body;
    a stiffening member adapted to be advanced within the lumen;
    an injection port adapted to deliver fluoro-visible media through the lumen to the body while the stiffening member is advanced within the lumen;
    a sealable member located at the distal end of the lumen to prevent fluids from the body from entering the lumen while allowing a distal end of the stiffening member to be advanced beyond a distal end of the lead body; and
    an inflatable member proximal to the electrode and adapted to be inflated prior to the delivery of fluoro-visible media through the lumen of the lead body.

2. The device of claim 1, wherein the sealable member is included within the electrode.

3. The device of claims 1 or 2, and further including a coiled conductor coupled to the electrode and extending to the proximal end of the lead body, wherein the coiled conductor defines the lumen.

4. The device of claim 3, wherein the coiled conductor is at least partially coated with an anti-inflammatory agent.

5. The device of claim 3, wherein the coiled conductor is at least partially coated with a lubricious coating to aid in the advancement of the stiffening member.

6. An implantable medical device for use in a body, comprising:
    an elongated lead body having a proximal end, a distal end, and a lumen;
    an electrode at the distal end of the lead body;
    a stiffening member adapted to be advanced within the lumen;
    an injection port adapted to deliver fluoro-visible media through the lumen to the body while the stiffening member is advanced within the lumen;
    a sealable member located at the distal end of the lumen to prevent fluids from the body from entering the lumen while allowing a distal end of the stiffening member to be advanced beyond a distal end of the lead body; and
    an inflatable member at the distal end of the lead body adapted to be inflated prior to the delivery of fluoro-visible media through the lumen of the lead body.

7. The device of claim 6, wherein the stiffening member is a guide wire including a lumen, and wherein the injection port is adapted to deliver fluoro-visible media through the lumen of the guide wire while the guide wire is advanced within the lumen of the lead body.

8. The device of claim 7, wherein at least a portion of the guide wire is coated with a lubricious material.

9. The device of claim 1, wherein the sealable member is a flexible membrane including at least one slit therein.

10. The device of claim 1, wherein the sealable member includes multiple flexible flap members.

11. The device of claim 10, wherein the multiple flexible flap members overlap.

12. The device of claim 1, wherein the sealable member is hinged to allow a preferential bending direction.

13. The device of claim 1, wherein the electrode includes a lumen aligned with the lumen of the lead body and open to the distal end of the lead; and
    wherein the sealable member is a generally cup-shaped resilient seal extending distally from the electrode.

14. The device of claim 13, wherein the electrode is further provided with an internal sleeve, mounted within the lumen of the lead body through the electrode, and to which the cup-shaped resilient seal is attached.

15. The device of claim 14, wherein the internal sleeve is provided with laterally directed bores and wherein the material of the resilient cup-shaped seal extends through the laterally extending bores to lock the seal to the sleeve.

16. The device of claim 14, wherein the internal sleeve is provided with a laterally extended ridge, engaging the cup-shaped resilient seal.

17. A method of delivering a medical device and a fluoro-visible media to a predetermined implant site within a body, comprising the steps of:

a.) advancing a stiffening member within a lumen of an elongated lead body;

b.) advancing the elongated lead body and stiffening member to a predetermined location within the body; and c.) utilizing the lumen of the lead body to deliver the fluoro-visible media to the body while the stiffening member is advanced within the lumen of the lead body, wherein step b.) includes advancing the elongated lead body and stiffening member within an inner lumen of an elongated sheath to the predetermined location within the body, and wherein step c.) further includes inflating an inflatable member located on a distal end of the lead body prior to delivering the fluoro-visible media.

18. The method of claim 17, wherein step d.) further includes the step of inflating an inflatable member located on the elongated lead body prior to delivering the fluoro-visible media.

19. The method of claim 17, wherein the stiffening member includes an inner lumen, and wherein step c.) includes delivering the fluoro-visible media to the body via the inner lumen of the stiffening member while the stiffening member is advanced within the lumen of the lead body.

20. The method of claim 19, wherein step c.) further includes the step of:

delivering the fluoro-visible media to the body via an opening of a sealable member provided at a distal end of the elongated lead body.

21. The method of claim 20, wherein the step of delivering the fluoro-visible media to the body via the opening of the sealable member is accomplished by advancing a distal end of the stiffening member through the opening of the sealable member before delivering the fluoro-visible media to the body via the inner lumen of the stiffening member.

22. The method of claim 20, wherein the step of delivering the fluoro-visible media to the body via the opening of the sealable member is accomplished by creating a pressure differential within an inner lumen of the body stiffening member.

23. The method of claim 17, wherein the stiffening member occupies only a portion of the lumen of the lead body, and wherein step c.) is performed by delivering the fluoro-visible media within a portion of the lumen of the lead body, not occupied by the stiffening member.

24. The method of claim 23, wherein the stiffening member has an outer diameter less than half the inner diameter of the lumen of the lead body, and wherein step c.) is performed by delivering the fluoro-visible media around the stiffening member located within the lumen of the lead body.

25. An implantable medical device for use in a body, comprising:

an elongated lead body having a proximal end, a distal end, and a lumen;

an injection port located at the distal end of the lead body and including a sealable member preventing fluid from entering the lumen through the injection port when the sealable member is in a normally closed position;

means for advancing the sealable member from the normally closed position to an open position to deliver fluoro-visible media through the lumen and the injection port to the body; and an inflatable member positioned along the distal end of the lead body and adapted to be inflated prior to the delivery of fluoro-visible media through the lumen of the lead body.

26. The device of claim 25, wherein the sealable member is a flexible membrane including at least one slit therein.

27. The device of claim 25, wherein the sealable member includes multiple flexible flap members.

28. The device of claim 27, wherein the multiple flexible flap members overlap.

29. The device of claim 25, wherein the sealable member is hinged to allow a preferential bending direction.

30. The device of claim 25, further comprising an electrode positioned along the distal end of the lead body, wherein the electrode includes an electrode lumen aligned with the lumen of the lead body and open to the distal end of the lead body, and wherein the sealable member is a generally cup-shaped resilient seal extending distally from the electrode.

31. The device of claim 30, wherein the electrode is further provided with an internal sleeve, mounted within the lumen of the lead body through the electrode, and to which the cup-shaped resilient seal is attached.

32. The device of claim 31 wherein the internal sleeve is provided with a laterally extended ridge, engaging the cup-shaped resilient seal.

33. The device of claim 25, wherein the means for advancing the sealable member creates a pressure differential within the lumen of the lead body.

34. The device of claim 25, wherein the means for advancing the sealable member is a stiffening member adapted to be advanced within the lumen.

* * * * *